(12) United States Patent
Hommeltoft

(10) Patent No.: US 9,193,653 B1
(45) Date of Patent: *Nov. 24, 2015

(54) ETHER LUBRICANTS FROM FATTY ACIDS

(71) Applicant: Sven Ivar Hommeltoft, Pleasant Hill, CA (US)

(72) Inventor: Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,459

(22) Filed: Nov. 13, 2014

(51) Int. Cl.
| | |
|---|---|
| *C07C 43/00* | (2006.01) |
| *C07C 41/01* | (2006.01) |
| *C07C 41/09* | (2006.01) |
| *C07C 41/06* | (2006.01) |
| *C07C 45/48* | (2006.01) |
| *C07C 29/145* | (2006.01) |

(52) U.S. Cl.
CPC ............... *C07C 41/01* (2013.01); *C07C 29/145* (2013.01); *C07C 41/06* (2013.01); *C07C 41/09* (2013.01); *C07C 45/48* (2013.01)

(58) Field of Classification Search
CPC .... C07C 29/143; C07C 29/145; C07C 45/48; C07C 41/26
USPC .......................... 568/687, 689, 697, 397, 881
See application file for complete search history.

(56) References Cited

U.S. PATENT DOCUMENTS

| | | |
|---|---|---|
| 7,074,972 B2 | 7/2006 | Maas et al. |
| 7,479,576 B1 | 1/2009 | Hassan et al. |
| 8,519,206 B2 | 8/2013 | Holtzapple et al. |
| 8,715,486 B2 | 5/2014 | Myllyoja et al. |

OTHER PUBLICATIONS

Nozawa et al. Cosmetics containing polyoxyethylene ethers, HCAPLUS document No. 90: 142064; Accession No. 1979: 142064 (1979).*

* cited by examiner

*Primary Examiner* — Sikarl Witherspoon
(74) *Attorney, Agent, or Firm* — Susan M. Abernathy

(57) ABSTRACT

Processes for producing long chain ethers from long chain secondary alcohols using fatty acid containing feedstocks. In an embodiment, a long chain secondary alcohol may be reacted with a primary alcohol, a secondary alcohol, or an olefin to form a long chain ether. In another embodiment, a long chain secondary alcohol or the corresponding alkoxide may be reacted with an alkyl halide to form a long chain ether. In yet a further embodiment, a long chain secondary alcohol may be converted to a halide, and the halide may be reacted with a second alcohol or the corresponding alkoxide to form a long chain ether. Long chain ether compositions of matter are also disclosed.

24 Claims, No Drawings

ETHER LUBRICANTS FROM FATTY ACIDS

TECHNICAL FIELD

This disclosure relates to processes for producing ether lubricants from fatty acids and to long chain ether compositions.

BACKGROUND

Some phenyl ethers have in the past been used as lubricants, but these typically have fairly high pour points and are not generally applied.

There is a need for long chain ether compositions for use as lubricants, and for processes for efficiently producing long chain ether lubricants from fatty acids or related feedstocks.

SUMMARY

In an embodiment there is provided a process comprising contacting at least one fatty acid with a ketonization catalyst in a ketonization zone under ketonization conditions to provide a long chain ketone according to the following Scheme 1:

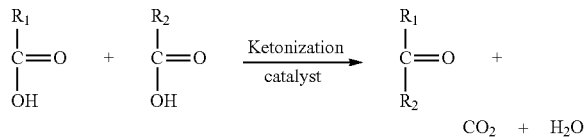

wherein $R_1$ and $R_2$ are independently selected from the group consisting of $C_5$-$C_{21}$ linear or branched alkyl and $C_5$-$C_{21}$ linear or branched alkenyl; contacting the long chain ketone with a selective ketone hydrogenation catalyst in a ketone hydrogenation zone in the presence of hydrogen gas under selective ketone hydrogenation conditions to provide a first long chain secondary alcohol according to the following Scheme 2:

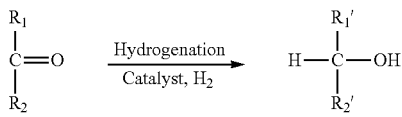

wherein: $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms; and reacting the first long chain secondary alcohol with a second alcohol or an olefin to form a long chain ether.

In another embodiment, there is provided at least one long chain ether product, or a product comprising a mixture of long chain ethers, prepared by processes as disclosed herein.

In a further embodiment there is provided a process comprising contacting at least one fatty acid with a ketonization catalyst in a ketonization zone under ketonization conditions to provide a long chain ketone according to the following Scheme 1:

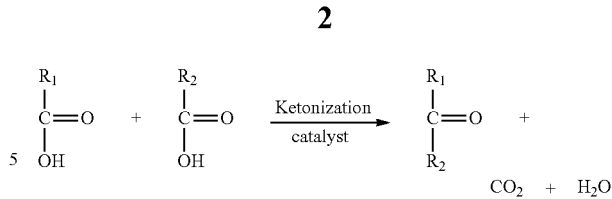

wherein $R_1$ and $R_2$ are independently selected from the group consisting of $C_5$-$C_{21}$ linear or branched alkyl and $C_5$-$C_{21}$ linear or branched alkenyl; contacting the long chain ketone with a selective ketone hydrogenation catalyst in a ketone hydrogenation zone in the presence of hydrogen gas under selective ketone hydrogenation conditions to provide a long chain secondary alcohol according to the following Scheme 2:

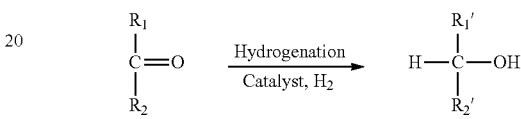

wherein: $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms; and reacting the long chain secondary alcohol, or a long chain alkoxide corresponding to the long chain secondary alcohol, with an alkyl halide to form a long chain ether according to the following Scheme 6:

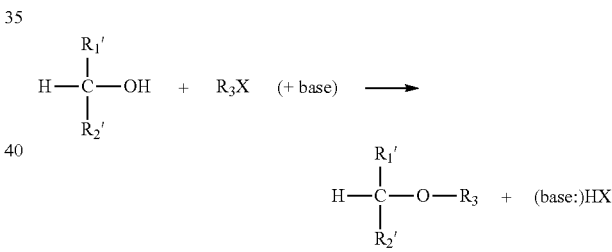

wherein: $R_3$ is selected from the group consisting of $C_1$-$C_{22}$ linear or branched alkyl and $C_2$-$C_{22}$ linear or branched alkenyl, and X is a halogen atom.

In yet another embodiment there is provided a process comprising contacting at least one fatty acid with a ketonization catalyst in a ketonization zone under ketonization conditions to provide a long chain ketone according to the following Scheme 1:

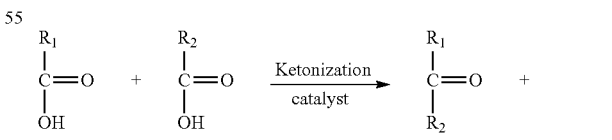

wherein $R_1$ and $R_2$ are independently selected from the group consisting of $C_5$-$C_{21}$ linear or branched alkyl and $C_5$-$C_{21}$ linear or branched alkenyl; contacting the long chain ketone with a selective ketone hydrogenation catalyst in a ketone hydrogenation zone in the presence of hydrogen gas under selective ketone hydrogenation conditions to provide a first long chain secondary alcohol according to the following Scheme 2:

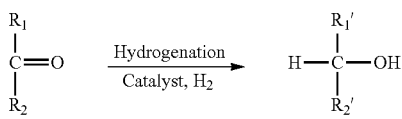

wherein: $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms; reacting the first long chain secondary alcohol with a halogenating agent to form a halide derivative of the first long chain secondary alcohol; and reacting the halide derivative of the first long chain secondary alcohol with a second alcohol, or with an alkoxide corresponding to the second alcohol, to form a long chain ether. The steps of reacting the first long chain secondary alcohol with the halogenating agent to form the halide derivative of the first long chain secondary alcohol and of reacting the halide derivative of the first long chain secondary alcohol with the second alcohol or the alkoxide corresponding to the second alcohol to form the long chain ether may be jointly performed according to the following Scheme 7:

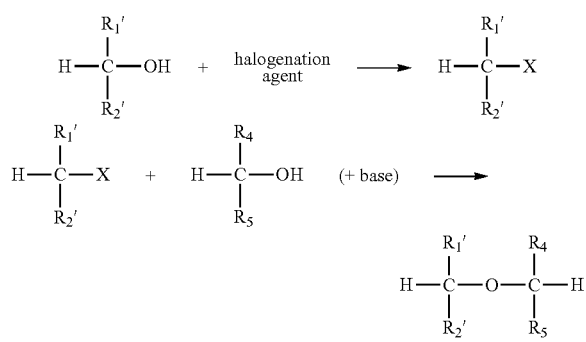

wherein $R_4$ and $R_5$ are independently selected from the group consisting of $C_1$-$C_{21}$ linear or branched alkyl and $C_2$-$C_{21}$ linear or branched alkenyl.

DETAILED DESCRIPTION

Conventional processes for preparing alcohols with a carbon chain length above that of available fatty acids are expensive. Also, such conventional processes place the alcohol group toward the end of the molecule. Also for lubricant applications, it may be important to prepare molecules with a sufficiently high boiling point and viscosity to meet specifications for most lubricant products. This typically requires carbon chains considerably longer than the $C_{16}$-$C_{18}$ chains that are made simply by hydrogenation of the most commonly available fatty acids and fatty oil feedstocks.

Applicant has demonstrated a new route to make long chain secondary alcohols, from fatty acids and fatty oils, in which the OH group may be placed non-terminally in the molecule and in which the carbon chain length is about twice (2×) the length of the carbon chain of alcohols prepared by simple hydrogenation of fatty acids and fatty oils. Furthermore, Applicant has discovered that long chain ethers may be prepared from the long chain secondary alcohols via a number of different routes. Such long chain ethers may find applications as lubricants.

Catalysts for Ketonization

In an embodiment, a suitable catalyst for ketonization may comprise alumina. In an embodiment, the ketonization catalyst may comprise at least 95 wt %, at least 99 wt %, or at least 99.5 wt % alumina. In an embodiment, the fresh ketonization catalyst may be calcined at a temperature in the range from 700 to 1100° F. (371 to 593° C.) for a time period in the range from 0.5 to 24 hours prior to contacting the ketonization catalyst with a reactant (long chain carboxylic acid or fatty acid). In an embodiment, the fresh ketonization catalyst may be calcined in the presence of steam. In an embodiment, the ketonization catalyst may comprise gamma alumina. In an embodiment, the ketonization catalyst may consist essentially of alumina.

In an embodiment, the surface area of the alumina catalyst for ketonization may be in the range from 15 to 500 m²/g of catalyst, or from 50 to 400 m²/g of catalyst, or from 100 to 250 m²/g of catalyst. In an embodiment, an alumina catalyst useful for ketonization reactions as disclosed herein may have various shapes including, for example, granules, pellets, spheres, extrudates, and the like. The alumina catalyst may be disposed within a ketonization zone. A ketonization zone is not limited to any particular reactor type. For example, a ketonization zone may use a fixed-, fluidized-, or moving bed reactor.

Over time, the ketonization catalyst may passivate and lose activity. An alumina catalyst that has become passivated to varying degrees following ketonization may be regenerated, e.g., as described in commonly assigned U.S. patent application Ser. No. 14/540,723, filed on even date herewith and entitled Ketonization process using oxidative catalyst regeneration.

Fatty Acid Ketonization

A ketone product may be prepared by contacting at least one fatty acid with a ketonization catalyst in a ketonization zone under ketonization conditions according to the following scheme (Scheme 1), wherein $R_1$ and $R_2$ are saturated or unsaturated aliphatic groups, and wherein $R_1$ and $R_2$ may be the same or different. As a non-limiting example, $R_1$ and $R_2$ may be independently selected from $C_5$-$C_{21}$ linear or branched alkyl and $C_5$-$C_{21}$ linear or branched alkenyl.

Scheme 1:

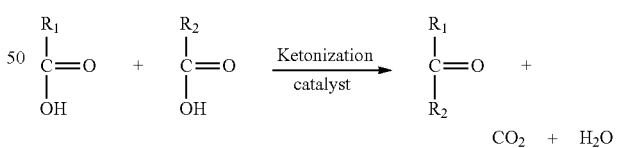

In a sub-embodiment, $R_1$ and $R_2$ may be independently selected from $C_7$-$C_{17}$ linear or branched alkyl or alkenyl, or from $C_9$-$C_{17}$ linear or branched alkyl or alkenyl, or from $C_9$-$C_{15}$ linear or branched alkyl or alkenyl, or from $C_{15}$-$C_{17}$ linear or branched alkyl or alkenyl. In an embodiment, ketonization may also be known as ketonic decarboxylation or fatty acid decarboxylation-coupling.

In an embodiment, the step of contacting the at least one fatty acid with the ketonization catalyst may comprise feeding a feedstock comprising the at least one fatty acid to the ketonization zone. In an embodiment, feedstocks for ketonization as disclosed herein may be derived from a triglyceride-containing biomass source such as oils or fats from plants and/or animals. In an embodiment, the feedstock may be obtained from biological material (e.g., fatty biomass) having a lipid content greater than (>) 30 wt % on a dry weight basis, or >50, or >70, or >90, or >95, or >99 wt % on a dry weight basis. In an embodiment, the biological material may comprises vegetable oil, animal tallow, algae, and combinations thereof. In an embodiment, the fatty acid feedstock may be derived from other, non-biomass, sources (e.g., Fischer-Tropsch synthesis). Such alternatively derived fatty acids may be mixed or blended with biomass derived fatty acids prior to ketonization, e.g., to alleviate logistical and/or supply related issues involving biomass.

In an embodiment, feedstocks for ketonization may comprise at least one fatty acid reactant or a mixture of fatty acid reactants. In an embodiment, the at least one fatty acid reactant for ketonization may comprise a mixture of at least two (2) fatty acids. In an embodiment, reactants for ketonization may comprise $C_6$-$C_{22}$ fatty acids and/or $C_6$-$C_{22}$ fatty acid derivatives. In an embodiment, such fatty acid derivatives may include $C_6$-$C_{22}$ fatty acid mono-, di-, and triglycerides, $C_6$-$C_{22}$ acyl halides, and $C_6$-$C_{22}$ salts of fatty acids. In a sub-embodiment, the fatty acids and/or fatty acid derivatives for ketonization may be in the range from $C_8$-$C_{18}$, or in the range from $C_{16}$-$C_{18}$. In an embodiment, at least one fatty acid for ketonization may be obtained from biological material, including various organisms and biological systems. In an embodiment, the at least one fatty acid may be obtained from at least one naturally occurring triglyceride, for example, wherein the triglyceride may be obtained from biomass. In an embodiment, feedstocks for ketonization may comprise at least 95 wt % fatty acids or at least 99 wt % fatty acids.

In an embodiment, reactants for ketonization may be derived from one or more triglyceride-containing vegetable oils such as, but not limited to, coconut oil, corn oil, linseed oil, olive oil, palm oil, palm kernel oil, rapeseed oil, safflower oil, soybean oil, sunflower oil, and the like. Additional or alternative sources of triglycerides, which can be hydrolyzed to yield fatty acids, include, but are not limited to, algae, animal tallow, and zooplankton.

In an embodiment, reactants for ketonization may include, without limitation, $C_8$-$C_{22}$ fatty acids, and combinations thereof. Examples of suitable saturated fatty acids may include, without limitation, caproic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), eicosanoic acid ($C_{20}$). Examples of unsaturated fatty acids may include, without limitation, palmitoleic acid, oleic acid, and linoleic acid. Reactants for ketonization may further include, without limitation, palm kernel oil, palm oil, coconut oil, corn oil, soy bean oil, rape seed (canola) oil, poultry fat, beef tallow, and their respective fatty acid constituents, and combinations thereof.

In an embodiment, the reactants for the ketonization reaction or step may be hydrogenated to substantially saturate some or all of the double bonds prior to ketonization. In cases where the fatty oils, i.e. triglycerides, are hydrolyzed to fatty acids, such saturation of the double bonds may be done before or after the hydrolysis.

In some aspects, wherein the above-mentioned hydrolyzed triglyceride sources contain mixtures of saturated fatty acids, mono-unsaturated fatty acids, and polyunsaturated fatty acids, one or more techniques may be employed to isolate, concentrate, or otherwise separate one or more types of fatty acids from one or more other types of fatty acids in the mixture (see, e.g., U.S. Pat. No. 8,097,740 to Miller).

Prior to contacting the reactant with the ketonization catalyst in the ketonization zone, the ketonization catalyst may be calcined. In an embodiment, the step of calcining the ketonization catalyst may be performed in the presence of steam. In an embodiment, the step of calcining the ketonization catalyst may be performed at a temperature in the range from 400 to 600° C., or from 450 to 500° C., for a time period in the range from 0.5 to 10 hours, or from 1 to 2 hours.

In an embodiment, a suitable catalyst for fatty acid ketonization may comprise alumina. In an embodiment, the ketonization catalyst may comprise substantially pure gamma alumina. In an embodiment, the ketonization catalyst may consist essentially of alumina.

Suitable ketonization conditions may include a temperature in the range from 100 to 500° C., or from 300 to 450° C.; a pressure in the range from 0.5 to 100 psi, or from 5 to 30 psi; and a liquid hourly space velocity (LHSV) in the range from 0.1 to 50 $h^{-1}$, or from 0.5 to 10 $h^{-1}$. In an embodiment, the partial pressure of the fatty acid in the ketonization zone may be maintained in the range of 0.1 to 30 psi. The ketonization process can be carried out in batch or continuous mode, with recycling of unconsumed starting materials if required.

In an embodiment, the decarboxylation reaction may be conducted in the presence of at least one gaseous- or liquid feedstock diluent. In an embodiment, the ketonization reaction may be carried out while the fatty acid is maintained in the vapor phase. Conditions for fatty acid ketonization are disclosed in commonly assigned U.S. patent application Ser. No. 13/486,097, filed Jun. 1, 2012, entitled Process for producing ketones from fatty acids. In an embodiment, a fatty acid reactant for the ketonization reaction may comprises a mixture of at least two (2) fatty acids such that the ketone product may comprise a mixture of at least three (3) different long chain ketones, each of which may be selectively hydrogenated to provide a mixture of at least three (3) different long chain secondary alcohols.

In an embodiment, the long chain ketones provided by the ketonization reaction can be separated from by-products (such as oligomeric or polymeric species and low molecular weight "fragments" from the fatty acid chains) by distillation. For example, in an embodiment the crude reaction product can be subjected to a distillation-separation at atmospheric or reduced pressure through a packed distillation column. In an embodiment, the ketonization product may be a wax under ambient conditions.

The long chain ketones produced from fatty acids, e.g., as disclosed hereinabove, may be converted to their corresponding long chain secondary alcohol by selective ketone hydrogenation over a selective ketone hydrogenation catalyst, e.g., as disclosed hereinbelow.

Catalysts for Selective Ketone Hydrogenation

A catalyst for the selective hydrogenation of long chain ketones to the corresponding secondary alcohols may be referred to herein as a "selective ketone hydrogenation catalyst." In an embodiment, the selective ketone hydrogenation catalyst for selective hydrogenation of long chain (e.g., $C_{11}$+) ketones may comprise a metal selected from Pt, Pd, Ru, Ni, Co, Mo, Cr, Cu, Rh, and combinations thereof. In an embodiment, the selective ketone hydrogenation catalyst may further comprise a support material. In an embodiment, the support material may be selected from carbon, silica, magnesia, titania, and combinations thereof. In an embodiment, at least some metal component(s) of the hydrogenation catalyst may be in elemental form. As a non-limiting example, the hydrogenation catalyst may comprise a metal selected from Pt, Pd, Ru, Ni, Rh, and combinations thereof, and the metal may be in elemental form in the hydrogenation catalyst. In a sub-embodiment, the hydrogenation catalyst may comprise a metal selected from Pt, Pd, and combinations thereof, and a support material comprising carbon, silica, magnesia, titania, and combinations thereof. In an embodiment, the hydrogenation catalyst may be unsupported meaning, for example, that the metal may be present either in finely divided form (e.g., as metal powder) or in pelletized or extruded or other structural form without the presence of a support material.

In an embodiment, the selective ketone hydrogenation catalyst lacks, or is devoid of, any component that promotes the dehydration of alcohols, such that the hydrogenation catalyst as a whole lacks catalytic activity for dehydration of the long chain secondary alcohol, under the conditions used for the selective hydrogenation of long chain ketones, such that ketone conversion to the corresponding alkene or alkane is prevented. Because the long chain ketones as disclosed herein exhibit comparatively low reactivity in the ketone hydrogenation reaction, e.g., in comparison with $C_3$ or $C_4$ ketones, more forcing conditions may be required for hydrogenation as compared to hydrogenation of lighter ketones; such (more forcing) conditions would be expected to exacerbate the negative effect on product selectivity of a hydrogenation catalyst having dehydration functionality. This highlights the significance of using a selective ketone hydrogenation catalyst, in processes as disclosed herein, for the efficient conversion of long chain ketones to the corresponding long chain secondary alcohols in high yield.

In an embodiment, a selective ketone hydrogenation catalyst will lack alumina. As an example, the selective ketone hydrogenation catalyst may be prepared without the use of an alumina component and with a support material, if any, lacking an alumina component, such that the selective ketone hydrogenation catalyst contains at most only trace amounts of alumina that are insufficient to be catalytically effective in dehydrating long chain secondary alcohols under the hydrogenation conditions as disclosed herein for the selective hydrogenation of long chain ketones to the corresponding secondary alcohols.

This is in stark contrast to conventional hydrotreating catalysts having alumina support material that is the major catalyst component by weight and volume. Applicant has observed that the presence of alumina, e.g., in conventional hydrotreating catalysts, negatively impacts the conversion of long chain ketones to the corresponding secondary alcohol product(s) as disclosed herein.

In an embodiment, the surface area of the hydrogenation catalyst may be in the range from 15 to 1000 $m^2/g$ of catalyst, or from 100 to 600 $m^2/g$ of catalyst, or from 250 to 450 $m^2/g$ of catalyst. In an embodiment a selective ketone hydrogenation catalyst, useful for selective hydrogenation of long chain ketones as disclosed herein, may have various shapes including, for example, powder, granules, pellets, spheres, extrudates, and the like. The selective ketone hydrogenation catalyst may be disposed within a ketone hydrogenation zone or ketone hydrogenation reactor. The ketone hydrogenation zone is not limited to any particular reactor type.

Long Chain Secondary Alcohols by Selective Hydrogenation of Long Chain Ketones

As described hereinabove, a long chain ketone may be prepared, e.g., according to Scheme 1 by contacting at least one fatty acid with a ketonization catalyst in a ketonization zone under ketonization conditions. The long chain ketone may then be selectively hydrogenated by contacting the long chain ketone with a selective ketone hydrogenation catalyst in a ketone hydrogenation zone under selective ketone hydrogenation conditions according to the following Scheme 2 to provide a long chain secondary alcohol.

Scheme 2:

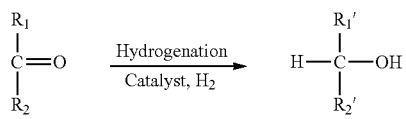

In Schemes 1 and 2, $R_1$ and $R_2$ may be the same or different, $R_1$ and $R_2$ may be independently selected from $C_5$-$C_{21}$ linear or branched alkyl and $C_5$-$C_{21}$ linear or branched alkenyl, wherein: when $R_1$ is alkyl $R_1'$=$R_1$, when $R_2$ is alkyl $R_2'$=$R_2$, when $R_1$ is alkenyl $R_1'$ is alkyl or alkenyl, when $R_2$ is alkenyl $R_2'$ is alkyl or alkenyl, and wherein $R_1$ and $R_1'$ have an equal number of carbon atoms, and $R_2$ and $R_2'$ have an equal number of carbon atoms. In an embodiment, $R_1'$ and $R_2'$ may be independently selected from $C_7$-$C_{17}$ linear or branched alkyl, or from $C_9$-$C_{17}$ linear or branched alkyl, or from $C_9$-$C_{15}$ linear or branched alkyl, or from $C_{15}$-$C_{17}$ linear or branched alkyl.

While not being bound by theory, in an embodiment wherein $R_1$ and $R_2$ are alkenyl, the product alcohol may be the corresponding saturated alcohol, since alkenyl group hydrogenation is typically more *facile* than ketone hydrogenation. As an example, when $R_1$ is alkenyl $R_1'$ may be alkyl, and when $R_2$ is alkenyl $R_2'$ may be alkyl. In a sub-embodiment, $R_1'$ and $R_2'$ may be independently selected from the group consisting of $C_5$-$C_{21}$ linear or branched alkyl.

In an embodiment, the at least one fatty acid may comprise a mixture of at least two (2) fatty acids, such that the long chain ketone prepared according to Scheme 1 may comprise a mixture of at least three (3) different long chain ketones, and the long chain secondary alcohol prepared according to Scheme 2 may similarly comprise a mixture of at least three (3) different long chain secondary alcohols.

In an embodiment, the selective ketone hydrogenation catalyst will lack catalytic activity for dehydration of the long chain secondary alcohol under the selective ketone hydrogenation conditions used such that, during the step of contacting the long chain ketone with the selective ketone hydrogenation catalyst, ketone conversion to the corresponding alkene or alkane is prevented or hindered. As a result, the corresponding secondary alcohol may be obtained from the long chain ketone with excellent selectivity (e.g., >80% selectivity at 90% conversion).

In an embodiment, a process for preparing long chain secondary alcohols may comprise avoiding contact of the at least one long chain ketone with alumina during the selective ketone hydrogenation step. For example, alumina promotes alcohol dehydration to alkenes, which may in turn be converted to alkanes during conventional hydrogenation, thereby substantially or greatly decreasing the yield of long chain secondary alcohols. Accordingly in an embodiment, the selective ketone hydrogenation catalyst as disclosed herein may be prepared without the use of alumina. In an embodiment, alumina or other material(s) that promote(s) alcohol dehydration may be specifically excluded from the selective ketone hydrogenation catalyst and the ketone hydrogenation zone.

In an embodiment, the selective ketone hydrogenation catalyst may comprise a metal selected from Pt, Pd, Ru, Ni, Co, Mo, Cr, Cu, Rh, and combinations thereof. In an embodiment, the hydrogenation catalyst may further comprise a support material selected from carbon, silica, magnesia, titania, and combinations thereof. In a sub-embodiment, the hydrogenation catalyst may comprise a metal selected from the group consisting of Pt, Pd, and combinations thereof, and a support material selected from carbon, silica, magnesia, titania, and combinations thereof.

In an embodiment, the ketone hydrogenation step may be performed in the absence of a material that promotes dehydration of the long chain secondary alcohol under the selective ketone hydrogenation conditions used, so as to prevent or hinder ketone conversion to the corresponding alkene or alkane, in order to greatly increase the selectivity of ketone conversion to the long chain secondary alcohol product. As a non-limiting example, the selective ketone hydrogenation step may be performed in the absence of alumina. Alumina is used as a catalyst support in conventional hydrotreating catalysts; however, processes as disclosed herein may involve avoiding the presence of alumina during ketone hydrogenation for the production of long chain secondary alcohols. In an embodiment, alumina may be avoided during the ketone hydrogenation step by using a selective ketone hydrogenation catalyst that lacks an alumina component. Selective ketone hydrogenation catalysts that lack alumina are described hereinabove.

In an embodiment, the selectivity of long chain ketone conversion to the corresponding long chain secondary alcohol via the selective ketone hydrogenation step (e.g., according to Scheme 2) may be much higher, e.g., typically at least about 15% higher, than that of comparable ketone hydrogenation in the presence of a conventional hydrotreating catalyst comprising alumina. As a non-limiting example, the selectivity of ketone conversion to the corresponding long chain secondary alcohol by a selective ketone hydrogenation catalyst as disclosed herein may be greater than (>) 80% at 90% conversion, whereas the selectivity of ketone conversion to the corresponding long chain secondary alcohol by a conventional hydrogenation catalyst comprising an alumina support is typically less than (<) 70% at 90% conversion.

In an embodiment, $R_1$ and $R_2$ in Schemes 1 and 2 may each be linear or branched alkyl. In a sub-embodiment, $R_1$ and $R_2$ may be independently selected from $C_5$-$C_{21}$ linear or branched alkyl, or from $C_7$-$C_{17}$ linear or branched alkyl, or from $C_9$-$C_{17}$ linear or branched alkyl, or from $C_9$-$C_{15}$ linear or branched alkyl, or from $C_{15}$-$C_{17}$ linear or branched alkyl. In an embodiment, the at least one long chain secondary alcohol formed by ketone hydrogenation, e.g., according to Scheme 2, may be in the range from $C_{11}$-$C_{43}$, or from $C_{21}$-$C_{31}$, or from $C_{31}$-$C_{35}$. In an embodiment, long chain secondary alcohols prepared by processes as disclosed herein may comprise a mixture of long chain secondary alcohols, e.g., each having from 11 to 43 carbon atoms per molecule. In an embodiment, each of the long chain secondary alcohols may have the hydroxyl group placed at a non-terminal location of the molecule. In a further embodiment, a long chain secondary alcohol prepared according to embodiments of processes disclosed herein may have the OH group placed at-or near the center of the secondary alcohol molecule.

In an embodiment, fatty acid ketonization may comprise contacting a mixture of at least two (2) fatty acids with the ketonization catalyst in the ketonization zone. In an embodiment, such a mixture of fatty acids may comprise a lipid mixture derived from a source of lipids selected from a plant, an animal, or other organism(s). Such sources of lipids may include, without limitation, terrestrial plants, mammals, microorganisms, aquatic plants, seaweed, algae, phytoplankton, and the like. In an embodiment, a mixture of fatty acids for ketonization according to processes as disclosed herein may be derived from palm kernel oil, palm oil, coconut oil, corn oil, soy bean oil, rape seed (canola) oil, poultry fat, beef tallow, and the like and their respective fatty acid constituents, and combinations thereof.

In another embodiment, a process for preparing a long chain secondary alcohol may comprise reacting a first fatty acid with a second fatty acid to form a long chain ketone, and selectively hydrogenating the long chain ketone to selectively form the corresponding secondary alcohol.

In an embodiment, the selectively hydrogenating step may comprise contacting the long chain ketone with a selective ketone hydrogenation catalyst in a ketone hydrogenation zone under selective ketone hydrogenation conditions. In an embodiment, the selective ketone hydrogenation catalyst will lack catalytic activity for dehydration of the secondary alcohol, under the selective ketone hydrogenation conditions used, such that ketone conversion to the corresponding alkene or alkane is prevented. Due to the relatively low reactivity of long chain ketones (e.g., $C_{11}$-$C_{43}$) in the ketone hydrogenation reaction, as compared with lighter ketones (e.g., $C_3$ or $C_4$), the more forcing conditions used for the long chain ketones would exacerbate the negative effect that a hydrogenation catalyst having dehydration functionality would have on product selectivity. Instead, the use of a selective ketone hydrogenation catalyst that at least substantially lacks dehydration activity, as disclosed herein, allows for the efficient conversion of long chain ketones with high selectivity to the corresponding long chain secondary alcohols.

In an embodiment, exemplary conditions for selective ketone hydrogenation may comprise a temperature in the range from 200 to 755° F. (93 to 402° C.), or from 355 to 755° F. (179 to 402° C.), or from 400 to 750° F. (204 to 399° C.), a pressure in the range from 200 to 5000 psi, or from 250 to 5000 psi, or from 300 to 4000 psi, a liquid hourly space velocity (LHSV) in the range from 0.05 to 5.0 $h^{-1}$, or from 0.1 to 5.0 $h^{-1}$, or from 0.5 to 4.0 $h^{-1}$, and a hydrogen to feed molar ratio in the range from 1.0 to 1000, or from 5.0 to 1000, or from 10 to 1000. In an embodiment, the hydrogenation catalyst may comprise a metal selected from the group consisting of Pt, Pd, Ru, Ni, Co, Mo, Cr, Cu, Rh, and combinations thereof. In a sub-embodiment, the metal may be selected from Pt, Pd, and combinations thereof.

As described hereinabove, the selective hydrogenation of long chain ketones may be performed in the absence of a material that promotes dehydration of the secondary alcohol under selective ketone hydrogenation conditions, such that conversion to the corresponding alkene or alkane is prevented or hindered. Accordingly, the selective ketone hydrogenation catalyst will lack a material, such as alumina, that promotes dehydration of the secondary alcohol under said selective ketone hydrogenation conditions. This is in contrast to conventional hydrotreating catalysts having an alumina support that promotes alcohol dehydration to alkenes, with subsequent hydrogenation to alkanes. Advantageously, selective ketone hydrogenation as disclosed herein allows the corresponding secondary alcohol to be obtained efficiently with excellent selectivity.

In an embodiment, long chain secondary alcohol product(s) prepared as disclosed herein may comprise a mixture of long chain secondary alcohols and may be subjected to various separation processes. Such separation may involve, for example, distilling and/or flash distillation to provide one or more long chain secondary alcohol products.

Long Chain Ethers Prepared from Long Chain Secondary Alcohols

In an embodiment, a process for preparing a long chain ether may comprise providing a long chain ketone, e.g., via fatty acid ketonization as described hereinabove according to Scheme 1, supra, and thereafter contacting the long chain ketone with a selective ketone hydrogenation catalyst under selective ketone hydrogenation conditions, e.g., as described hereinabove, to provide a first long chain secondary alcohol according to the following Scheme 2:

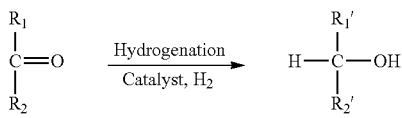

wherein $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms. In an embodiment, $R_1'$ and $R_2'$ may be independently selected from the group consisting of $C_5$-$C_{21}$ linear or branched alkyl and $C_5$-$C_{21}$ linear or branched alkenyl. Thereafter, the first long chain secondary alcohol may be reacted with a second alcohol or an olefin to form a long chain ether.

Catalysts and conditions for fatty acid ketonization and long chain ketone selective hydrogenation are described, e.g., hereinabove. In an embodiment, the at least one fatty acid for the ketonization reaction (Scheme 1, supra) may comprise a mixture of at least two (2) fatty acids, and the long chain ether (e.g., as represented by general Formula I, infra) may comprise a mixture of at least three (3) long chain ethers. In an embodiment, a long chain ether prepared as disclosed herein may be in the range from $C_{26}$-$C_{86}$, or from $C_{35}$-$C_{86}$, or from $C_{35}$-$C_{70}$.

As noted hereinabove, in an embodiment the long chain ether may be prepared by reacting the first long chain secondary alcohol with a second alcohol. In an embodiment, the step of reacting the first long chain secondary alcohol with the second alcohol may comprise contacting the first long chain secondary alcohol with the second alcohol in the presence of an acidic catalyst. Non-limiting examples of acidic catalysts that may be used when reacting the long chain secondary alcohol with a second alcohol include: sulfuric acid, phosphoric acid, fluorosulfonic acid, perfluoro alkane sulfonic acids, methanesulfonic acid, toluenesulfonic acid, and acidic ion exchange resins such as Amberlyst® 15 or Nafion®, as well as solid acid catalysts such as acidic zeolites, sulfated zirconia and tungstated zirconia.

Suitable conditions for reacting the first long chain secondary alcohol with the second alcohol may vary, for example, depending on the catalyst and the reactants. Typically the reaction conditions may include a temperature in the range from 100 to 350° C., or from 120 to 200° C., and a pressure in the range from 0.01 psi to 500 psi, or from atmospheric pressure to 100 psi. In an embodiment, the reaction may be conducted under conditions that allow for the removal of liberated water by azeotropic distillation.

In an embodiment, the second alcohol may be a primary alcohol, and the step of reacting the first long chain secondary alcohol with the second alcohol may be according to the following Scheme 3:

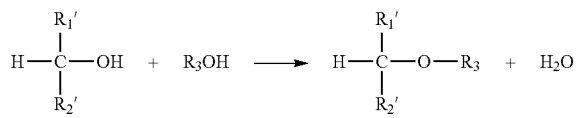

wherein $R_1'$ and $R_2'$ may be independently selected from $C_5$-$C_{21}$ linear or branched alkyl and $C_5$-$C_{21}$ linear or branched alkenyl, and $R_3$ is selected from $C_1$-$C_{22}$ linear or branched alkyl and $C_2$-$C_{22}$ linear or branched alkenyl. In an embodiment, the second alcohol may be a $C_1$-$C_{22}$ primary alcohol. In a sub-embodiment, the second alcohol may be a short chain alcohol, such as methanol ethanol, or n-propanol.

In an embodiment, the second alcohol may be a second secondary alcohol, and the step of reacting the first long chain secondary alcohol with the second alcohol may be according to the following Scheme 4:

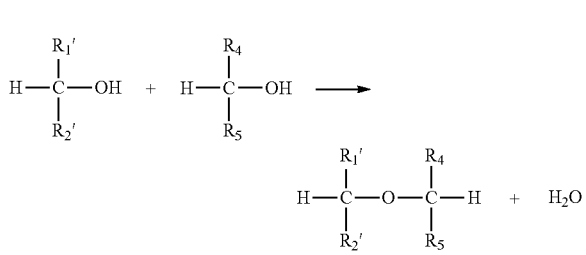

wherein $R_1'$ and $R_2'$ may be independently selected from $C_5$-$C_{21}$ linear or branched alkyl and $C_5$-$C_{21}$ linear or branched alkenyl, wherein $R_4$ and $R_5$ are independently selected from $C_1$-$C_{21}$ linear or branched alkyl and $C_2$-$C_{21}$ linear or branched alkenyl, and $R_4$ and $R_5$ are the same or different.

In an embodiment, the second alcohol may be a second long chain secondary alcohol prepared according to the fatty acid ketonization and long chain ketone hydrogenation steps as described, e.g., with reference to Schemes 1 and 2, for the preparation of the first long chain secondary alcohol. In another embodiment, the second alcohol may be a short chain alcohol, such as isopropanol.

According to another embodiment, a long chain ether may be prepared by reacting a long chain secondary alcohol with an olefin according to the following Scheme 5:

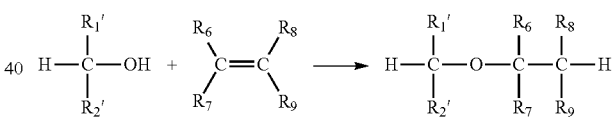

wherein $R_1'$ and $R_2'$ may be independently selected from $C_5$-$C_{21}$ linear or branched alkyl and $C_5$-$C_{21}$ linear or branched alkenyl; $R_6$ is selected from $C_1$-$C_{40}$ linear or branched alkyl; $R_7$, $R_8$, and $R_9$ are independently selected from a hydrogen atom and $C_1$-$C_{21}$ linear or branched alkyl; and $R_7$, $R_8$, and $R_9$ are the same or different. In an embodiment, $R_6$ may be the same as at least one of $R_7$, $R_8$, and $R_9$. Typically, $R_6$ will be different from one or more of $R_7$, $R_8$, and $R_9$. In a sub-embodiment, $R_6$ may be selected from $C_1$-$C_{40}$ linear or branched alkyl and $R_7$ may be a hydrogen atom.

In an embodiment, the step of reacting a long chain secondary alcohol with an olefin may comprise contacting the long chain secondary alcohol with the olefin in the presence of an acidic catalyst. Non-limiting examples of acidic catalysts that may be used when reacting the long chain secondary alcohol with an olefin include: sulfuric acid, phosphoric acid, fluorosulfonic acid, perfluoro alkane sulfonic acids, methanesulfonic acid, toluenesulfonic acid, and acidic ion exchange resins such as Amberlyst® 15 or Nafion®, as well as solid acid catalysts such as acidic zeolites, sulfated zirconia and tungstated zirconia.

Suitable conditions for reacting the first long chain secondary alcohol with the olefin may vary, for example, depending on the catalyst and the reactants. Typically the reaction conditions may include a temperature in the range from 100 to 350° C., or from 150 to 250° C., and a pressure in the range from atmospheric pressure to 500 psi.

In an embodiment, the long chain secondary alcohol in Scheme 5 may be prepared by fatty acid ketonization and long chain ketone selective hydrogenation, e.g., as described with reference to Schemes 1 and 2, supra.

In an embodiment, the olefin in Scheme 5 may be a tertiary olefin. In another embodiment, the olefin in Scheme 5 may be a secondary olefin. In an embodiment, the olefin can be either internal or terminal (alpha olefin). In a sub-embodiment, the olefin may be a non-conjugated diene. In an embodiment, the olefin may be in the range from $C_4$-$C_{10}$, or from $C_4$-$C_5$. Non-limiting examples of olefins that may be used in Scheme 5 include isobutene and isopentenes.

In another embodiment, the olefin in Scheme 5 may be an olefin oligomer. In an embodiment, such an olefin oligomer may be prepared from a material selected from $C_3$-$C_5$ olefins and combinations thereof. In an embodiment, the olefin oligomer may have from 6 to 50 carbon atoms, or from 9 to 50 carbon atoms. In an embodiment, the olefin may be a propylene oligomer.

A process for preparing a long chain ether according to another embodiment may comprise providing a long chain secondary alcohol. In an embodiment, the long chain secondary alcohol may itself be prepared by providing a long chain ketone, e.g., as described hereinabove according to Scheme 1, supra; and contacting the long chain ketone with a selective ketone hydrogenation catalyst under selective ketone hydrogenation conditions, e.g., as described hereinabove according to Scheme 2. Thereafter, the long chain secondary alcohol, or a long chain alkoxide corresponding to the long chain secondary alcohol, may be reacted with an alkyl halide to form a long chain ether according to the following Scheme 6:

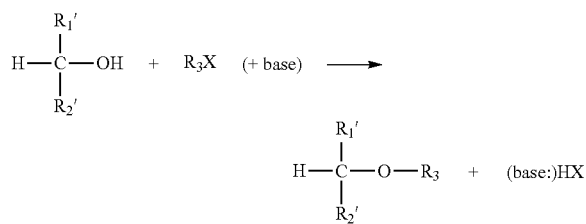

wherein $R_1'$ and $R_2'$ may be independently selected from $C_5$-$C_{21}$ linear or branched alkyl and $C_5$-$C_{21}$ linear or branched alkenyl, wherein $R_3$ is selected from $C_1$-$C_{22}$ linear or branched alkyl and $C_2$-$C_{22}$ linear or branched alkenyl, and X is a halogen atom. In an embodiment, the reaction of the long chain secondary alcohol, or the corresponding alkoxide, with the alkyl halide may be performed in the presence of a base.

In an embodiment, such process may comprise converting (deprotonating) the long chain secondary alcohol (e.g., Scheme 6) to the corresponding long chain alkoxide; and thereafter the long chain alkoxide may be reacted with the alkyl halide, e.g., essentially according to Scheme 6. In an embodiment, the corresponding long chain alkoxide may be in the form of an alkali metal alcoholate. In an embodiment, the deprotonation reaction to produce the alkali metal alcoholate from the corresponding alcohol may be performed either by reacting the alcohol with a strong base, such as sodium hydride or sodium isopropoxide or potassium tert-butoxide, or with an alkali metal, such as sodium or potassium.

In an embodiment, a long chain ether prepared according to Scheme 6 may be in the range from $C_{26}$-$C_{86}$, or from $C_{35}$-$C_{86}$, or from $C_{35}$-$C_{70}$. In an embodiment, a long chain ether product prepared according to processes as disclosed herein may comprise a mixture of two or more long chain ethers.

According to a further embodiment of a process for preparing a long chain ether from a first long chain secondary alcohol, the first long chain secondary alcohol may itself be prepared from a long chain ketone, wherein the long chain ketone may be prepared e.g., as described hereinabove according to Scheme 1, supra, and the long chain ketone may be contacted with a selective ketone hydrogenation catalyst under selective ketone hydrogenation conditions to provide the first long chain secondary alcohol, e.g., as described hereinabove according to Scheme 2, supra. Thereafter, the first long chain secondary alcohol may be reacted with a halogenating agent to form a halide derivative of the first long chain secondary alcohol; and the halide derivative of the first long chain secondary alcohol may be reacted with a second alcohol, or with an alkoxide corresponding to the second alcohol, to form a long chain ether according to the following Scheme 7:

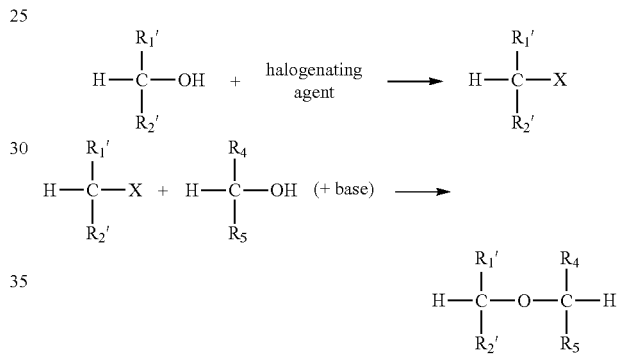

wherein $R_1'$ and $R_2'$ may be independently selected from $C_5$-$C_{21}$ linear or branched alkyl and $C_5$-$C_{21}$ linear or branched alkenyl, wherein $R_4$ and $R_5$ are independently selected from $C_1$-$C_{21}$ linear or branched alkyl and $C_2$-$C_{21}$ linear or branched alkenyl.

Non-limiting examples of halogenating agents for forming the halide derivative of the long chain secondary alcohol include hydrogen halide, HX, wherein X is selected from Cl, Br, and I) and thionyl halide, $SOX_2$, wherein X is selected from Cl and Br. The halogenation may be performed in the absence of a catalyst or in the presence of a catalyst. For thionyl halide, such catalyst may be a weak base such as pyridine. For the HX addition, anhydrous $ZnX_2$ or $CaX_2$ will in some cases promote the replacement of the alcohol group with the halide.

In an embodiment, the halide derivative of the first long chain secondary alcohol may be reacted with the alkoxide corresponding to the second alcohol. In an embodiment, the second alcohol may be a short chain alcohol, such as isopropanol. In another embodiment, the second alcohol may comprise a second long chain secondary alcohol. In a sub-embodiment, the second long chain secondary alcohol may be prepared according to Schemes 1 and 2, supra. In an embodiment, a long chain ether prepared according to Scheme 7 may be in the range from $C_{26}$-$C_{86}$, or from $C_{35}$-$C_{86}$, or from $C_{35}$-$C_{70}$. In an embodiment, long chain ether products prepared according to Scheme 7 may be in the bright stock range.

According to another embodiment, there is provided a composition comprising a long chain ether of general Formula I:

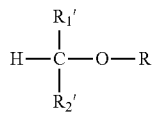

wherein $R_1'$ and $R_2'$ may be independently selected from $C_5$-$C_{21}$ linear or branched alkyl and $C_5$-$C_{21}$ linear or branched alkenyl, wherein $R_1'$ and $R_2'$ are the same or different, and R is selected from linear or branched alkyl having up to 52 carbon atoms and linear or branched alkenyl having up to 52 carbon atoms.

In an embodiment of a composition according to general Formula I, $R_1'$ and $R_2'$ may be independently selected from $C_5$-$C_{21}$ linear or branched alkyl. In a sub-embodiment of a composition according to general Formula I, $R_1'$ and $R_2'$ may be independently selected from $C_7$-$C_{17}$ linear or branched alkyl.

In another embodiment of a composition according to general Formula I, R may be selected from $C_1$-$C_{22}$ linear or branched alkyl and $C_2$-$C_{22}$ linear or branched alkenyl. In a sub-embodiment, R may be selected from $C_1$-$C_{22}$ linear alkyl, or from $C_1$-$C_{12}$ linear alkyl, or from $C_1$-$C_6$ linear alkyl.

In an embodiment of a composition according to general Formula I, R may have partial structure II:

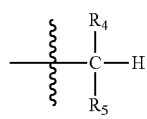

wherein $R_4$ and $R_5$ are independently selected from $C_1$-$C_{21}$ linear or branched alkyl and $C_2$-$C_{21}$ linear or branched alkenyl, and wherein $R_4$ and $R_5$ may be the same or different.

In another embodiment of a composition according to general Formula I, R may have partial structure III:

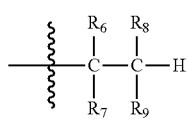

wherein $R_6$ may be selected from $C_1$-$C_{40}$ linear or branched alkyl, and wherein $R_7$, $R_8$, and $R_9$ are independently selected from a hydrogen atom and $C_1$-$C_{22}$ linear or branched alkyl.

With further reference to structure III, in an embodiment $R_6$, $R_7$, $R_8$, and $R_9$ may jointly contain from 3 to 50 carbon atoms. In an embodiment, a long chain ether of general Formula I may be in the range from $C_{26}$-$C_{86}$, or from $C_{35}$-$C_{86}$, or from $C_{35}$-$C_{70}$.

In an embodiment, a long chain ether of general Formula I may have a Viscosity Index greater than (>) 120, or in the range from 120 to 150. In an embodiment, the long chain ether composition disclosed herein may comprise a mixture of at least two different long chain ether compounds of general Formula I. Such a mixture of long chain ethers of general Formula I may exhibit improved cold flow properties, in comparison with individual component ethers of such a mixture.

According to another embodiment, there is provided a composition comprising a long chain ether of general Formula IV:

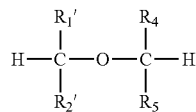

wherein $R_1'$ and $R_2'$ may be independently selected from $C_5$-$C_{21}$ linear or branched alkyl and $C_5$-$C_{21}$ linear or branched alkenyl, wherein $R_1'$ and $R_2'$ are the same or different, and wherein $R_4$ and $R_5$ are independently selected from $C_1$-$C_{21}$ linear or branched alkyl and $C_2$-$C_{21}$ linear or branched alkenyl, and $R_4$ and $R_5$ are the same or different.

With further reference to Formula IV, in a sub-embodiment $R_1'$ and $R_2'$ may be independently selected from $C_5$-$C_{21}$ linear or branched alkyl. In another sub-embodiment, $R_1'$ and $R_2'$ may be independently selected from $C_7$-$C_{17}$ linear or branched alkyl. In yet another sub-embodiment, $R_4$ and $R_5$ may be independently selected from $C_7$-$C_{17}$ linear or branched alkyl. In an embodiment, a long chain ether of general Formula IV may have a Viscosity Index greater than (>) 120, or in the range from 120 to 150.

According to a further embodiment, there is provided a composition comprising a long chain ether of general Formula V:

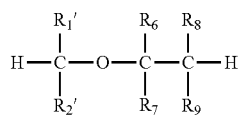

wherein $R_1'$ and $R_2'$ may be independently selected from $C_5$-$C_{21}$ linear or branched alkyl and $C_5$-$C_{21}$ linear or branched alkenyl, and wherein $R_1'$ and $R_2'$ are the same or different, wherein $R_6$ is selected from $C_1$-$C_{40}$ linear or branched alkyl, and $R_7$, $R_8$, and $R_9$ are independently selected from a hydrogen atom and $C_1$-$C_{22}$ linear or branched alkyl.

With further reference to Formula V, in a sub-embodiment $R_1'$ and $R_2'$ may be independently selected from $C_5$-$C_{21}$ linear or branched alkyl. In another sub-embodiment, $R_1'$ and $R_2'$ may be independently selected from $C_7$-$C_{17}$ linear or branched alkyl. In an embodiment, $R_6$, $R_7$, $R_8$, and $R_9$ may jointly contain from 3 to 50 carbon atoms. In an embodiment, a long chain ether of general Formula V may have a Viscosity Index greater than (>) 120, or in the range from 120 to 150.

In an embodiment, the long chain ether(s) prepared as disclosed herein may comprise a mixture of two or more long chain ether compounds. In an embodiment, long chain ether product(s) prepared as disclosed herein, e.g., comprising a mixture of long chain ethers, may be subjected to various separation processes. Such separation may involve, for example, distilling and/or flash distillation to provide one or more long chain ether products.

Distilling

In an embodiment, a step of distilling may employ one or more distillation columns to separate the desired product(s) from by-products. In an embodiment, the step of distilling may employ flash distillation or partial condensation techniques to remove by-products including at least low molecular weight materials. Those of skill in the art will recognize that there is some flexibility in characterizing the high and low boiling fractions, and that the products may be obtained from "cuts" at various temperature ranges.

EXAMPLES

Example 1

Ketonization of Lauric Acid to Laurone Using Alumina Catalyst

The ketonization of lauric acid to 12-tricosanone (laurone) was catalyzed by an alumina catalyst operated in a fixed bed continuously fed reactor at ambient pressure, at a temperature range of 770-840° C., and with a feed rate that gave a liquid hourly space velocity (LHSV) of 0.62-0.64 h$^{-1}$. The conversion rate of lauric acid to laurone was calculated based on the composition of the product as determined by GC analysis using an FID detector.

The freshly loaded new alumina catalyst was calcined in the reactor at 900° F. (482° C.) with a stream of dry nitrogen (2 volumes of nitrogen per volume of catalyst per minute) for 2 hours before the temperature was lowered to 770° F. (410° C.), nitrogen was turned off and the lauric acid feed was introduced. Product composition analysis showed that the fresh catalyst operating at 770° F., LHSV=0.62-0.64 h$^{-1}$, gave a lauric acid conversion of 62-66%.

Example 2

Hydrogenation of 12-tricosanone to 12-tricosanol Over a Pt/Carbon Hydrogenation Catalyst 12-tricosanone (Example 1) was hydrogenated over a carbon supported platinum catalyst to make the corresponding alcohol, 12-tricosanol, as follows. 12-tricosanone was introduced as a liquid flow (4.1-4.4 g/hr, 12-13 mmoles/hr) together with hydrogen (100 Nml/min, 250 mmoles/hr) to a fixed reactor holding 7 ml of 0.5% Pt/carbon (3.5 g, particle size: 0.3-1 mm). The pressure was held at 1500 psi. The liquid products were collected after the reaction and analyzed by GC. The liquid product stream was found to contain three components: unconverted 12-tricosanone and two products: the target alcohol, 12-tricosanol, and the corresponding n-alkane, n-tricosane, of which the latter was present only in trace amounts.

At 450-470° F. reaction temperature the GC analysis of the product showed a conversion of 12-tricosanone of 80-87% and a selectivity to 12-tricosanol of 98.9-99.4% with the remaining 0.6-1.1% being n-tricosane formed by hydro-deoxygenation of the alcohol.

Example 3

Preparation of 12-tricosanyl n-butyl ether 40.3 g (0.118 mole) 12-tricosanol (Example 2) was heated with 3.0 g (0.13 mole, 10% molar excess) sodium metal to 130° C. for a period of 15 hrs during which most of the sodium dissolved with hydrogen evolution to form the corresponding alkoxide, sodium 12-tricosanolate, which is liquid at 130° C. The thus prepared sodium 12-tricosanolate was subsequently treated with 20 ml (0.19 mole, 60% molar excess) n-butyl chloride in the presence of 20 ml THF at 90° C. for 7 days. The resulting reaction mixture was quenched with aqueous sodium hydroxide and extracted with heptane. The heptane solution was cooled to 20° F. during which 8.9 g of solid precipitate (unconverted 12-tricosanol and 12-tricosanone) formed and was removed. The heptane was evaporated at 80° C., 10 torr to yield the 12-tricosanyl n-butyl ether (33.2 g) as a colorless oil having the following properties: VI=147, VIS100=2.768 cSt, VIS40=9.395, cloud point: −3° C., pour point: −4° C.

Example 4

Preparation of 12-tricosanyl sec-butyl ether 12-tricosanyl sec-butyl ether was prepared from sodium 12-tricosanolate using a procedure analogous to that of Example 3. The properties of the thus prepared 12-tricosanyl sec-butyl ether were as follows: VI=130, VIS100=2.874 cSt, VIS40=10.36 cSt. (Cloud point and pour point were not measure but the product freezes around −2° C.)

Example 5

Preparation of 12-tricosanyl n-octyl ether 12-tricosanyl n-octyl ether was prepared from sodium 12-tricosanolate using a procedure analogous to that of Example 3. The properties of the thus prepared 12-tricosanyl n-octyl ether were as follows: VI=148, VIS100=3.247 cSt, VIS40=11.89 cSt, Pour point=−14° C., cloud point=−4° C.

The reaction of sodium metal with a long chain secondary alcohol, such as 12-tricosanol and heavier, may typically be relatively slow even at a temperature of about 130° C. A faster way to make a long chain sodium alcoholate is by reaction of the long chain alcohol with a solution of an alcoholate of a lighter secondary or tertiary alcohol to form the corresponding long chain alkoxide and the lighter alcohol; the lighter alcohol may then be subsequently removed by evaporation. Thus, 12-tricosanolate may be made by treating 12-tricosanol with a solution of 1 equivalent of sodium isopropylate in anhydrous isopropanol to form sodium 12-tricosanolate, as described in Example 6, infra. The sodium 12-tricosanolate may be subsequently reacted with an alkyl halide to form a long chain ether as described hereinabove.

Example 6

Preparation of Sodium 12-tricosanolate Using Sodium Isopropanolate in Isopropanol Solution 3.1 g (0.135 mole) sodium metal was dissolved in 40 ml isopropanol under reflux conditions for 4 hrs to make a solution of sodium isopropanolate in isopropanol. 47 g (0.138 mole) 12-tricosanol was added and the resulting isopropanol was subsequently evaporated by heating to 170-180° C. for 2 hrs to yield the sodium 12-tricosanolate for further reaction.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Additionally, chemical species including reactants and products designated by a numerical range of carbon atoms include any one or more of, or any combination of, or all of the chemical species within that range.

Any term, abbreviation or shorthand not defined is understood to have the ordinary meaning used by a person skilled in the art at the time the application is filed. The singular forms "a," "an," and "the," include plural references unless expressly and unequivocally limited to one instance. All publications, patents, and patent applications cited in this application are incorporated by reference herein in their entirety to the extent not inconsistent herewith.

Modifications of the exemplary embodiments disclosed above may be apparent to those skilled in the art in light of this disclosure. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:
1. A process, comprising:
   a) contacting at least one fatty acid with a ketonization catalyst in a ketonization zone under ketonization conditions to provide a long chain ketone according to the following Scheme 1:

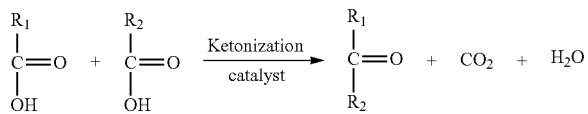

wherein $R_1$ and $R_2$ are independently selected from the group consisting of $C_5$-$C_{21}$ linear or branched alkyl and $C_5$-$C_{21}$ linear or branched alkenyl;
   b) contacting the long chain ketone with a selective ketone hydrogenation catalyst in a ketone hydrogenation zone in the presence of hydrogen gas under selective ketone hydrogenation conditions to provide a first long chain secondary alcohol according to the following Scheme 2:

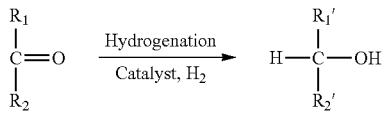

wherein:
   $R_1$ and $R_2$ are the same or different,
   when $R_1$ is alkyl $R_1'=R_1$,
   when $R_2$ is alkyl $R_2'=R_2$,
   when $R_1$ is alkenyl $R_1'$ is alkyl or alkenyl,
   when $R_2$ is alkenyl $R_2'$ is alkyl or alkenyl,
   $R_1$ and $R_1'$ have an equal number of carbon atoms, and
   $R_2$ and $R_2'$ have an equal number of carbon atoms; and
   c) reacting the first long chain secondary alcohol with a second alcohol or an olefin to form a long chain ether.
2. The process according to claim 1, wherein step c) comprises contacting the first long chain secondary alcohol with the second alcohol in the presence of an acidic catalyst.
3. The process according to claim 1, wherein the second alcohol is a primary alcohol, and step c) comprises reacting the first long chain secondary alcohol with the second alcohol according to the following Scheme 3:

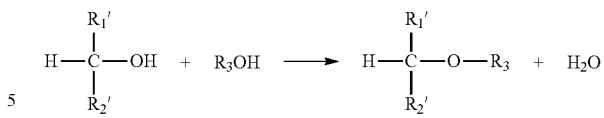

wherein:
   $R_1'$ and $R_2'$ are as defined in claim 1, and
   $R_3$ is selected from the group consisting of $C_1$-$C_{22}$ linear or branched alkyl and $C_2$-$C_{22}$ linear or branched alkenyl.
4. The process according to claim 1, wherein the second alcohol is a second secondary alcohol, and step c) comprises reacting the first long chain secondary alcohol with the second alcohol according to the following Scheme 4:

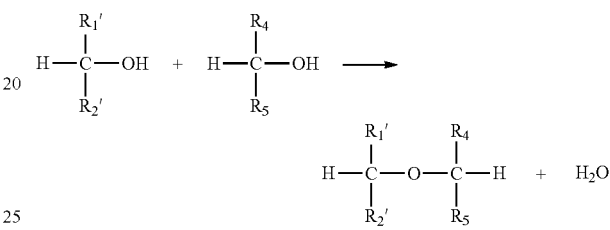

wherein:
   $R_1'$ and $R_2'$ are as defined in claim 1,
   $R_4$ and $R_5$ are independently selected from the group consisting of $C_1$-$C_{21}$ linear or branched alkyl and $C_2$-$C_{21}$ linear or branched alkenyl, and
   $R_4$ and $R_5$ are the same or different.
5. The process according to claim 1, wherein the second alcohol is a second long chain secondary alcohol prepared according to steps a) and b).
6. The process according to claim 1, wherein step c) comprises reacting the first long chain secondary alcohol with the olefin according to the following Scheme 5:

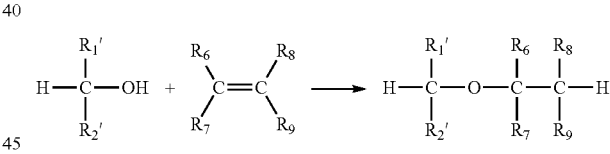

wherein:
   $R_1'$ and $R_2'$ are as defined in claim 1,
   $R_6$ is selected from the group consisting of $C_1$-$C_{40}$ linear or branched alkyl, and
   $R_7$, $R_8$, and $R_9$ are independently selected from the group consisting of a hydrogen atom and $C_1$-$C_{21}$ linear or branched alkyl, and
   $R_7$, $R_8$, and $R_9$ are the same or different.
7. The process according to claim 1, wherein the olefin is a tertiary olefin.
8. The process according to claim 1, wherein:
   the olefin is an olefin oligomer prepared from a material selected from the group consisting of $C_3$-$C_5$ olefins and combinations thereof, and
   the olefin oligomer has from 6 to 50 carbon atoms.
9. The process according to claim 1, wherein:
   the ketonization catalyst consists essentially of alumina, and
   the selective ketone hydrogenation catalyst comprises a metal selected from the group consisting of Pt, Pd, Ru, Ni, Cr, Cu, Rh, and combinations thereof, and a support material selected from the group consisting of carbon, silica, magnesia, titania, and combinations thereof.

10. The process according to claim 1, wherein said selective ketone hydrogenation conditions comprise a temperature in the range from 200 to 755° F., a pressure in the range from 200 to 5000 psi, a LHSV in the range from 0.05 to 5.0 hr$^{-1}$, and a hydrogen to feed molar ratio in the range from 1.0 to 1000.

11. The process according to claim 1, wherein:
the at least one fatty acid comprises a mixture of at least two (2) fatty acids, and
the long chain ether comprises a mixture of at least three (3) long chain ethers.

12. The process according to claim 1, wherein the long chain ether is in the range from $C_{26}$-$C_{86}$.

13. The long chain ether prepared according to the process of claim 3, and having a structure of:

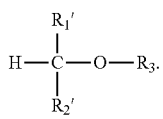

14. A process, comprising:
a) contacting at least one fatty acid with a ketonization catalyst in a ketonization zone under ketonization conditions to provide a long chain ketone according to the following Scheme 1:

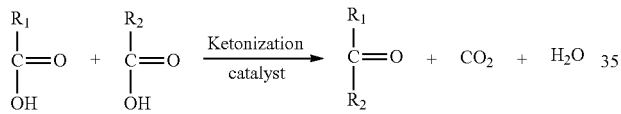

wherein $R_1$ and $R_2$ are independently selected from the group consisting of $C_5$-$C_{21}$ linear or branched alkyl and $C_5$-$C_{21}$ linear or branched alkenyl,
b) contacting the long chain ketone with a selective ketone hydrogenation catalyst in a ketone hydrogenation zone in the presence of hydrogen gas under selective ketone hydrogenation conditions to provide a long chain secondary alcohol according to the following Scheme 2:

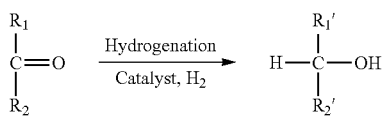

wherein:
$R_1$ and $R_2$ are the same or different,
when $R_1$ is alkyl $R_1'$=$R_1$,
when $R_2$ is alkyl $R_2'$=$R_2$,
when $R_1$ is alkenyl $R_1'$ is alkyl or alkenyl,
when $R_2$ is alkenyl $R_2'$ is alkyl or alkenyl,
$R_1$ and $R_1'$ have an equal number of carbon atoms, and
$R_2$ and $R_2'$ have an equal number of carbon atoms; and
c) reacting the long chain secondary alcohol, or a long chain alkoxide corresponding to the long chain secondary alcohol, with an alkyl halide to form a long chain ether according to the following Scheme 6:

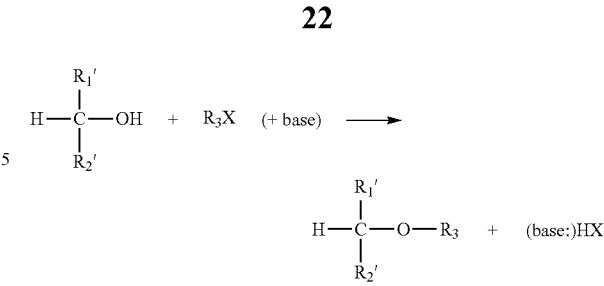

wherein:
$R_3$ is selected from the group consisting of $C_1$-$C_{22}$ linear or branched alkyl and $C_2$-$C_{22}$ linear or branched alkenyl, and
X is a halogen atom.

15. The process according to claim 14, further comprising:
d) converting the long chain secondary alcohol to the corresponding long chain alkoxide, and wherein step c) comprises reacting the long chain alkoxide with the alkyl halide.

16. The process according to claim 14, wherein the long chain ether is in the range from $C_{26}$-$C_{86}$.

17. The long chain ether prepared according to the process of claim 16, wherein $R_1'$ and $R_2'$ are independently selected from the group consisting of $C_5$-$C_{21}$ linear or branched alkyl, and having a structure of

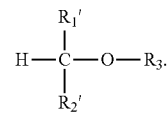

18. A process, comprising:
a) contacting at least one fatty acid with a ketonization catalyst in a ketonization zone under ketonization conditions to provide a long chain ketone according to the following Scheme 1:

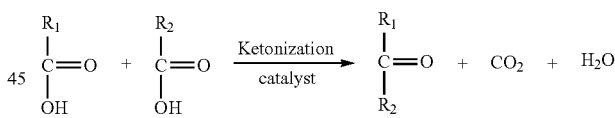

wherein $R_1$ and $R_2$ are independently selected from the group consisting of $C_5$-$C_{21}$ linear or branched alkyl and $C_5$-$C_{21}$ linear or branched alkenyl;
b) contacting the long chain ketone with a selective ketone hydrogenation catalyst in a ketone hydrogenation zone in the presence of hydrogen gas under selective ketone hydrogenation conditions to provide a first long chain secondary alcohol according to the following Scheme 2:

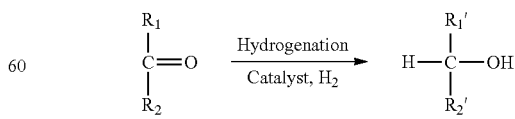

wherein:
$R_1$ and $R_2$ are the same or different,
when $R_1$ is alkyl $R_1'$=$R_1$,
when $R_2$ is alkyl $R_2'$=$R_2$, when $R_1$ is alkenyl $R_1'$ is alkyl or alkenyl,
when $R_2$ is alkenyl $R_2'$ is alkyl or alkenyl,
$R_1$ and $R_1'$ have an equal number of carbon atoms, and
$R_2$ and $R_2'$ have an equal number of carbon atoms;

c) reacting the first long chain secondary alcohol with a halogenating agent to form a halide derivative of the first long chain secondary alcohol; and d) reacting the halide derivative of the first long chain secondary alcohol with a second alcohol, or with an alkoxide corresponding to the second alcohol, to form a long chain ether, wherein steps c) and d) are jointly performed according to the following Scheme 7:

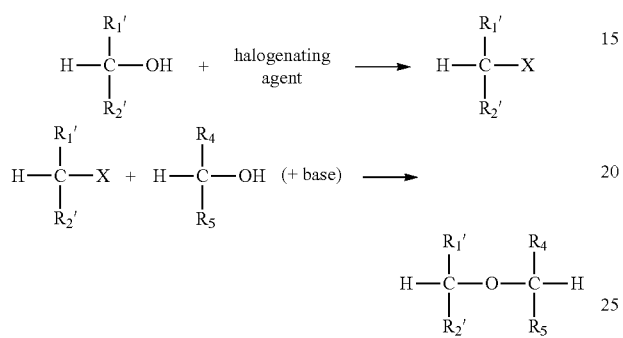

wherein $R_4$ and $R_5$ are independently selected from the group consisting of $C_1$-$C_{21}$ linear or branched alkyl and $C_2$-$C_{21}$ linear or branched alkenyl.

19. The process according to claim 18, wherein:
the second alcohol comprises a second long chain secondary alcohol prepared according to steps a) and b), and
step d) comprises reacting the halide derivative of the first long chain secondary alcohol with the alkoxide corresponding to the second alcohol.

20. The long chain ether prepared according to the process of claim 18, wherein $R_1'$ and $R_2'$ are independently selected from the group consisting of $C_5$-$C_{21}$ linear or branched alkyl, and having a structure of

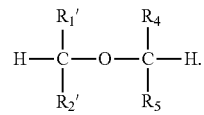

21. The long chain ether prepared according to the process of claim 4, and having a structure of:

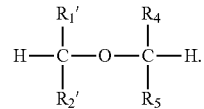

22. The long chain ether prepared according to the process of claim 6, and having a structure of:

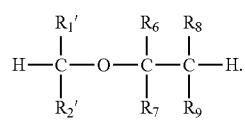

23. The long chain ether prepared according to the process of claim 1, wherein the long chain ether is a lubricant having a Viscosity Index greater than 120.

24. The process of claim 1, wherein the long chain ether is used as a lubricant.

* * * * *